(12) United States Patent
Kuster et al.

(10) Patent No.: US 10,729,480 B2
(45) Date of Patent: Aug. 4, 2020

(54) EXPANDABLE FASTENER FOR ORTHOPAEDIC APPLICATIONS

(71) Applicant: CURTIN UNIVERSITY, Bentley (AU)

(72) Inventors: Markus Kuster, Bentley (AU);
Matthew Peter Oldakowski, Bentley (AU); Intan Camellia Watono Oldakowska, Bentley (AU); Garry Allison, Bentley (AU); Gabriel Lee, City Beach (AU)

(73) Assignee: CURTIN UNIVERSITY, Bentley (AU)

( * ) Notice: Subject to any disclaimer, the term of this patent is extended or adjusted under 35 U.S.C. 154(b) by 0 days.

(21) Appl. No.: 16/085,064

(22) PCT Filed: Mar. 20, 2017

(86) PCT No.: PCT/AU2017/050248
§ 371 (c)(1),
(2) Date: Sep. 14, 2018

(87) PCT Pub. No.: WO2017/156596
PCT Pub. Date: Sep. 21, 2017

(65) Prior Publication Data
US 2019/0083152 A1    Mar. 21, 2019

(30) Foreign Application Priority Data
Mar. 18, 2016    (AU) .................................. 2016901033

(51) Int. Cl.
*A61B 17/84*    (2006.01)
*A61B 17/86*    (2006.01)
(Continued)

(52) U.S. Cl.
CPC ............ *A61B 17/844* (2013.01); *A61B 17/04* (2013.01); *A61B 17/0401* (2013.01);
(Continued)

(58) Field of Classification Search
CPC .... A61B 2017/0412; A61B 2017/0427; A61B 2017/0429; A61B 2017/043;
(Continued)

(56) References Cited

U.S. PATENT DOCUMENTS

| | | | |
|---|---|---|---|
| 3,693,616 | A | 9/1972 | Roaf et al. |
| 4,041,939 | A | 8/1977 | Hall |

(Continued)

FOREIGN PATENT DOCUMENTS

| | | |
|---|---|---|
| CN | 201719362 U | 1/2011 |
| DE | 32 21 835 A1 | 1/1984 |

(Continued)

OTHER PUBLICATIONS

International Search Report dated May 31, 2017 in International application No. PCT/AU2017/050248, 5 pages.

(Continued)

*Primary Examiner* — Larry E Waggle, Jr.
(74) *Attorney, Agent, or Firm* — Foley & Lardner LLP

(57) ABSTRACT

The present disclosure provides an expandable fastener for orthopaedic applications and arranged for fastening when positioned in a bore hole in bone. The fastener comprises a body having an axis. The fastener further comprises an expansion portion moveable between a contracted configuration and an expanded configuration such that, in use, the expansion portion urges outwardly from the body towards the bone surrounding the bore hole. The fastener is arranged such that ingrowth of bone between the expansion portion and the body is substantially avoided when the expansion portion is in the expanded configuration.

16 Claims, 16 Drawing Sheets

(51) Int. Cl.
*A61B 17/04* (2006.01)
*A61B 17/72* (2006.01)
*A61B 17/00* (2006.01)

(52) U.S. Cl.
CPC ...... *A61B 17/7233* (2013.01); *A61B 17/7258* (2013.01); *A61B 17/7266* (2013.01); *A61B 17/866* (2013.01); *A61B 17/8625* (2013.01); *A61B 17/8685* (2013.01); *A61B 2017/00862* (2013.01); *A61B 2017/00889* (2013.01); *A61B 2017/043* (2013.01); *A61B 2017/044* (2013.01); *A61B 2017/0412* (2013.01); *A61B 2017/0429* (2013.01); *A61B 2017/0432* (2013.01); *A61B 2017/0435* (2013.01); *A61B 2017/0445* (2013.01); *A61B 2017/8655* (2013.01)

(58) Field of Classification Search
CPC .... A61B 2017/0432; A61B 2017/0435; A61B 17/7233; A61B 17/7258; A61B 17/7266; A61B 17/844; A61B 2017/8655; A61B 17/8685; A61B 2017/00889
See application file for complete search history.

(56) References Cited

U.S. PATENT DOCUMENTS

| | | | |
|---|---|---|---|
| 4,047,524 A | 9/1977 | Hall | |
| 4,716,893 A * | 1/1988 | Fischer | A61B 17/686 606/309 |
| 4,776,851 A | 10/1988 | Bruchman et al. | |
| 5,030,220 A | 7/1991 | Howland | |
| 5,092,866 A | 3/1992 | Breard et al. | |
| 5,282,863 A | 2/1994 | Burton | |
| 5,375,823 A | 12/1994 | Navas | |
| 5,480,401 A | 1/1996 | Navas | |
| 5,540,688 A | 7/1996 | Navas | |
| 5,713,904 A | 2/1998 | Errico et al. | |
| 5,954,722 A | 9/1999 | Bono | |
| 6,290,700 B1 | 9/2001 | Schmotzer | |
| 6,299,613 B1 | 10/2001 | Ogilvie et al. | |
| 6,511,481 B2 | 1/2003 | Von Hoffmann | |
| 6,689,135 B2 | 2/2004 | Enayati | |
| 7,867,264 B2 * | 1/2011 | McDevitt | A61B 17/0401 606/313 |
| 8,043,340 B1 | 10/2011 | Law | |
| 8,105,360 B1 | 1/2012 | Connor | |
| 8,926,611 B2 | 1/2015 | Keller | |
| 9,452,003 B2 | 9/2016 | Voor | |
| 10,279,086 B2 * | 5/2019 | Harris | A61L 31/16 |
| 2002/0007184 A1 | 1/2002 | Ogilvie et al. | |
| 2002/0173791 A1 | 11/2002 | Howland | |
| 2004/0034353 A1 | 2/2004 | Michelson | |
| 2005/0101956 A1 | 5/2005 | Simonson | |
| 2006/0247635 A1 | 11/2006 | Gordon et al. | |
| 2007/0162002 A1 | 7/2007 | Tornier | |
| 2007/0162003 A1 | 7/2007 | Tornier et al. | |
| 2007/0162004 A1 | 7/2007 | Tornier et al. | |
| 2008/0183209 A1 | 7/2008 | Robinson et al. | |
| 2009/0005821 A1 * | 1/2009 | Chirico | A61B 17/8625 606/319 |
| 2009/0105759 A1 | 4/2009 | Gimbel et al. | |
| 2009/0224023 A1 | 9/2009 | Moskowitz et al. | |
| 2009/0287249 A1 | 11/2009 | Reynolds et al. | |
| 2010/0036496 A1 | 2/2010 | Yu et al. | |
| 2010/0094358 A1 | 4/2010 | Moore et al. | |
| 2010/0152790 A1 | 6/2010 | Hestad | |
| 2010/0324606 A1 | 12/2010 | Moskowitz et al. | |
| 2010/0324607 A1 | 12/2010 | Davis | |
| 2011/0152935 A1 | 6/2011 | Fortin et al. | |
| 2011/0160774 A1 | 6/2011 | Malek | |
| 2011/0208312 A1 | 8/2011 | Moskowitz et al. | |
| 2011/0218571 A1 | 9/2011 | Attia | |
| 2011/0251644 A1 | 10/2011 | Hestad et al. | |
| 2011/0295320 A1 | 12/2011 | Jackson | |
| 2011/0295323 A1 | 12/2011 | Hudgins et al. | |
| 2011/0307017 A1 | 12/2011 | Veldman et al. | |
| 2011/0313461 A1 | 12/2011 | Prevost et al. | |
| 2011/0319935 A1 | 12/2011 | Moskowitz et al. | |
| 2012/0010714 A1 | 1/2012 | Moskowitz et al. | |
| 2012/0016421 A1 | 1/2012 | Zylber et al. | |
| 2012/0016422 A1 | 1/2012 | Hua | |
| 2012/0046696 A1 | 2/2012 | Winslow et al. | |
| 2012/0078373 A1 | 3/2012 | Gamache et al. | |
| 2015/0045841 A1 * | 2/2015 | Oglaza | A61B 17/686 606/322 |

FOREIGN PATENT DOCUMENTS

| | | |
|---|---|---|
| DE | 42 39 716 C1 | 8/1994 |
| EP | 0 669 109 A1 | 8/1995 |
| EP | 0 919 199 B | 1/2005 |
| EP | 1 364 622 B1 | 7/2005 |
| EP | 1 952 775 A2 | 8/2008 |
| EP | 1 970 031 A2 | 9/2008 |
| EP | 2 404 563 A1 | 1/2012 |
| EP | 2 430 994 A2 | 3/2012 |
| EP | 2 921 142 A1 | 9/2015 |
| FR | 2799949 A1 | 4/2001 |
| FR | 2827498 A1 | 1/2003 |
| GB | 2 382 304 A | 5/2003 |
| JP | 2002-224131 A | 8/2002 |
| KR | 20080016586 A | 2/2008 |
| TW | 200843691 A | 11/2008 |
| WO | WO-98/22033 A1 | 5/1998 |
| WO | WO-01/45576 A1 | 6/2001 |
| WO | WO-2006/037384 A1 | 4/2006 |
| WO | WO-2006/045091 A2 | 4/2006 |
| WO | WO-2006/135511 A1 | 12/2006 |
| WO | WO-2006/136937 A2 | 12/2006 |
| WO | WO-2008/000944 A2 | 1/2008 |
| WO | WO-2008/073447 A2 | 6/2008 |
| WO | WO-2008/132322 A2 | 11/2008 |
| WO | WO-2009/009772 A1 | 1/2009 |
| WO | WO-2009/115663 A2 | 9/2009 |
| WO | WO-2010/018317 A1 | 2/2010 |
| WO | WO-2010/053785 A1 | 5/2010 |
| WO | WO-2010/091549 A1 | 8/2010 |
| WO | WO-2010/108333 A1 | 9/2010 |
| WO | WO-2012/006064 A1 | 1/2012 |
| WO | WO-2012/024807 A1 | 3/2012 |

OTHER PUBLICATIONS

Written Opinion of the International Searching Authority dated May 31, 2017 in International application No. PCT/AU2017/050248, 5 pages.

Search Report dated Oct. 16, 2019 received in corresponding European application No. 17 76 5588.3, 7 pages.

* cited by examiner (a)

(b)

(c)

(a)

(b)

EXPANDABLE FASTENER FOR ORTHOPAEDIC APPLICATIONS

CROSS-REFERENCE TO RELATED APPLICATIONS

The present application is a U.S. National Stage of International Application No. PCT/AU2017/050248 filed on Mar. 20, 2017, which claims the benefit of Australian Patent Application No. 2016901033, filed on Mar. 18, 2016, the entire disclosures of all of which are incorporated herein by reference.

FIELD OF THE INVENTION

The present invention relates to an expandable fastener for orthopaedic applications.

BACKGROUND OF THE INVENTION

Expandable fasteners in bore holes in bone have been used in the past for orthopaedic applications in order to increase fixation strength and decrease the risk of failures.

It is usually required to remove the fasteners from the bore holes after a period of time, which requires contracting the fasteners from an expanded configuration to a contracted configuration. However, ingrowth of bone often makes it impossible to contract the fasteners, which results in complications.

SUMMARY OF THE INVENTION

The present invention provides an expandable fastener for orthopaedic applications and arranged for fastening when positioned in a bore hole in bone, the fastener comprising:
 a body having an axis; and
 an expansion portion moveable between a contracted configuration and an expanded configuration such that, in use, the expansion portion urges outwardly from the body towards the bone surrounding the bore hole;
  wherein the fastener is arranged such that ingrowth of bone between the expansion portion and the body is substantially avoided when the expansion portion is in the expanded configuration.

The fastener may be arranged such that, when the fastener is in the expanded configuration, the expansion member is in contact with the body along at least a majority of a length of the expansion portion.

In one specific embodiment of the present invention the expansion portion contacts the body along the length and typically also across the width of the expansion portion whereby the fastener is arranged such that a gap between the expansion portion and the body is substantially avoided.

The expansion portion may be partially or entirely surrounded by the body when the expansion portion is in the expanded configuration. A gap, or any gap, between the expansion portion and the body may be sufficiently small such that ingrowth of bone is substantially or entirely avoided when the fastener is in the expanded configuration.

In one specific example any immediately adjacent surface regions of the expansion portion and the body are in direct contact with each other such that a gap between the adjacent surface regions is substantially avoided.

The fastener may also be arranged such that ingrowth of bone along the axis of the body is substantially avoided when the fastener is in the expanded configuration.

In one specific embodiment of the present invention the fastener is arranged such that at least a portion of a thickness of the expansion portion overlaps with a portion of the body along a length of the expansion portion when the fastener is in the expanded configuration.

In another specific embodiment of the present invention the fastener comprises an element arranged to cover or fill at least a portion of a gap between the expansion portion and the body when the fastener is in the expanded configuration. In this specific embodiment at least some or all immediately adjacent surface regions of the expansion portion and the body are in indirect contact via the element.

The expansion portion may be a part of an expansion member that is separate from the body. Alternatively, the expansion portion may be attached to the body.

In one specific embodiment the expansion portion is one of a plurality of expansion portions. In this embodiment the expansion portions are typically attached to the body.

The element may be arranged to cover or fill at least a portion of a gap between adjacent expansion portions.

The expansion portions may be positioned at different angular positions around an axis of the fastener. Further, at least some of the expansion portions may be positioned at different longitudinal positions or levels along the axis of the fastener. In addition, at least some of the expansion portions may be positioned at substantially the same longitudinal position along the axis of the fastener.

At least a portion of the length of the expansion portion may comprise a threaded or corrugated outer surface.

Further, the expansion portion may have an end surface that is substantially arc shaped.

The expansion portion may have wedge-shaped contact surfaces that extend along at least a portion of the length of the expansion portion and wedge against the body at contact surfaces of the body when the fastener is in the expanded configuration.

Alternatively or additionally, the body may have wedge-shaped contact surfaces that extend along at least a portion of the length of the expansion portion and wedge against the expansion portion at contact surfaces of the expansion portion when the fastener is in the expanded configuration.

The expansion portion may have an actuating surface and the fastener may be arranged such that the expansion portion is urged outwardly away from the axis of the fastener when an actuating member is received along the axis and urges against the actuating surface. The fastener may comprise the actuating member.

The actuating surface may be convexly shaped or may have a projection or the like. Alternatively, the actuating surface may have an indentation or may be concave and arranged such that the actuating member actuates within the indentation or within the concave shaped surface whereby the fastener is arranged such that an overlap between the body and the expansion portion is increased for a given expansion of the expansion portion compared with an expansion portion that has a convexly shaped actuating surface and is thinner at side surfaces of the expansion portion.

In one specific embodiment the expansion portion is part of an expansion member that is moveable relative to the body along an axis of the body. In this embodiment the expansion member is typically not attached to the body. The fastener may also comprise an actuating element. The actuating element may be positioned at a distal end of the fastener and the fastener may be arranged such that the expansion member is moveable towards or away from the actuating element along the axis of the body. Further, the fastener may be arranged such that, when the expansion member is moved towards the distal end of the fastener and towards the actuating element and engages with the actuating element, further movement of the expansion member towards the actuating element urges the expansion portion of the expansion member away from the axis of the body and forwardly to transfer the fastener into an expanded configuration and provide a penetrating force into the bone.

In one variation the actuating element has a tapered surface that has an apex and is positioned to facilitate an outward urging of the expansion portion of the expansion member when the expansion portion of the expansion member contacts the tapered surface of the actuating element, and when the expansion member is further moved toward the actuating element.

In another embodiment the fastener comprises an actuating member that is separate from the body and is moveable along the axis of the body. The fastener may be arranged such that the expansion portion urges outwardly away from the axis of the body when an actuating member is received along the axis and urges against the actuating surface portion of the expansion portion.

The expansion portion may be one of a plurality of expansion portions and at least two expansion portions may be oriented in opposite directions. When in the expanded configuration, the at least two expansion portions oriented in opposite directions and urged outwardly present the advantage that the fixation strength of the fastener may be increased where the surrounding bone is hard and dense.

In one embodiment the fastener comprises at least two pairs of expansion portions. In this embodiment the expansion portions of one pair are oriented opposite to the expansion portions of the other pair such that ends of the expansion portions of one pair oppose ends of the expansion portions of the other pair. A first pair of expansion portions may be attached to the body and a second pair of expansion portions may be separate from the body. The expansion portions of both pairs may be arranged to urge outwardly when the ends of the expansion portions of one pair are moved against the opposing ends of the other pair. In this embodiment, the fastener may be arranged such that an actuating member, moveable along the axis of the body, can move the ends of the expansion portions of one pair that are against the opposing ends of the other pair. The fastener may be arranged such that the ends of both pairs of expansion portions urge outwardly in a manner such that a gap between the opposing ends of the expansion portions is substantially avoided.

Further, the fastener may be arranged such that elastic forces caused by an inwardly urging first pair of expansion portions against the second pair of expansion portions facilitate removal of the fastener when in the expanded condition and when the actuating member is removed.

The expansion portion may comprise a bending region at which the expansion portion predominantly bends when the expansion portion urges towards the expanded configuration and the bending region may be positioned inside an outer periphery of the body and may be at least partially overlapped by a portion of the body.

At least portions of the body or the expansion portion may comprise an outer deformable layer of a material, and may be arranged such that, when the expansion portion urges outwardly, contact surfaces of the body or sidewalls of the expansion portion fractionally engage with each other thereby allowing the outer deformable layer of material to deform and fill or overlap at least a portion of a gap that may otherwise form between the expansion portion and the body. The outer deformable layer of the material may comprise titanium.

The fastener may be formed using a 3D printing process such as a process including Selective Laser Melting or Electron Beam Melting.

The fastener may comprise an outer elastic layer, such as an elastic membrane. The elastic membrane may be arranged to overlay gaps that may form between the body and an expansion portion or between adjacent expansion portions when in the expanded configuration and thereby avoid ingrowth of bone. The elastic layer or membrane may or may not be separate from the body and the expansion portion and may surround both the body and the expansion portion.

The fastener may also comprise a material that may be non-viscous and may be positioned between the body and the expansion portion or between adjacent expansion portions so as to fill a gap. For example, the material may initially be injected into an interior portion and may be positioned to penetrate into a gap between the body and the expansion portion or between adjacent expansion portions when the actuator is received by the fastener and urges the expansion portion or the expansion portions outwardly.

A deformable material may be infused into an interior of the fastener and may comprise an antibacterial substance arranged to substantially prevent formation or accumulation of bacteria. The deformable material may also be used to fill a gap along the axis of the body when the fastener is in the expanded configuration. The deformable material may comprise a polymeric material such as rubber.

Alternatively or additionally, the fastener may also comprise a coating that has chemical properties that substantially inhibit or reduce growth of bone at the coating such that the ingrowth of bone between the expansion portion and the body is reduced when the fastener is in the expanded configuration.

The fastener is typically formed from bio-compatible materials.

The fastener may be arranged such that the expansion member urges inwardly when an actuating member is removed.

If the expansion portion fails to contract when the fastener should be removed, the fastener may be arranged such that contraction of the expansion portion can be triggered. For example, the fastener may comprise a removal element arranged to engage with the expansion portion wherein the removal element is arranged to contract the expansion portion when removal of the fastener from the bore hole in bone is initiated.

The fastener may comprise a removal element arranged for insertion into the body and structured to engage with the expansion portion when the fastener is in the expanded configuration wherein the removal element is arranged to contract the expansion portion when the removal element is moved in a direction away from the bore hole along an axis of the fastener.

In one example the removal element is attached to, or part of, the body, and the fastener is arranged such that, when the expansion portion is moved along the axis of the body, the expansion portion is moved inwardly.

Alternatively, the removal element may be part of, or may be coupled to, another device (such as a plate, an intramedullary nail or a rod), and the fastener may be arranged such that, when the removal element with the other device is moved along the axis of the body, the expansion portion urges inwardly if not fully contracted.

The removal element may be a spring element or an elastic element that urges the expansion portion inwardly when the actuating member is removed. For example, the spring element or elastic element may be provided in the form of an elastic ring, or spring clip that surrounds at least a portion of the fastener.

The fastener may comprise an actuating element that also functions as a removal element.

One of the expansion portion and the actuating element may comprise a hole and the other one of the expansion portion and the actuating element may comprise a suitable projection for engagement within the hole. Either one or both of the hole and the projection may be tapered in a manner to facilitate engagement.

The actuating element and the expansion portion may be arranged such that the actuating member engages with the expansion portion and forces the expansion portion to move from an expanded to a contracted configuration when the actuating element is moved in a direction away from the bore hole along an axis of the fastener. The actuating element may comprise a central rod that is coupled to the expansion portion via a linkage, wherein the fastener is arranged and the linkage is positioned such that the expansion portion moves between the contracted configuration and the expanded configuration when the actuation element moves to different positions along the axis of the fastener.

The body of the fastener may have a threaded or corrugated outer surface along at least a portion of its length.

The expansion portion may have a thickness that is tapered in a direction around the axis of the fastener such that, when the expansion portion is in the expanded configuration, the expansion portion projects at one side portion further away from the axis than at an opposite second side portion.

A person skilled in the art will appreciate that the fastener may be used for various orthopaedic applications.

For example, the fastener may be used for bone fracture fixation and spine fixation, or as intramedullary nail and hip stems.

BRIEF DESCRIPTION OF THE FIGURES

Embodiments of the present invention will now be described, by way of example only, with reference to the accompanying Figures, in which.

DETAILED DESCRIPTION OF SPECIFIC EMBODIMENTS

Figure 1:
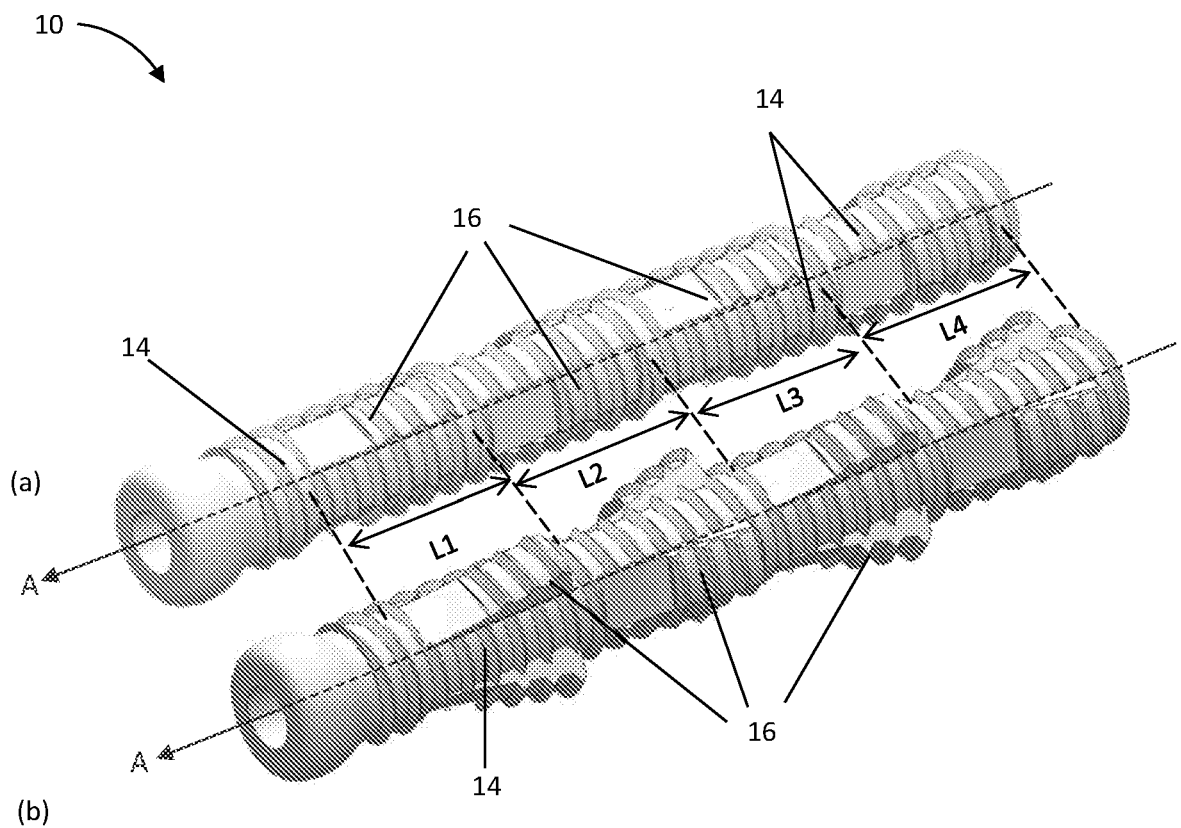
FIGS. 1 (a) and (b) show a fastener in accordance with an embodiment of the present invention.

Embodiments of the present invention generally relate to an expandable fastener. For example, the fastener may be used for orthopaedic applications to secure stabilisation members used to stabilise fractured bones. The fastener is arranged for positioning in a bore hole in bone.

The fastener has a body and expansion portions that are moveable between a contracted and an expanded configuration such that, in use, the expansion portions urge outwardly from the body towards the bone surrounding the bore hole. The fastener is arranged such that ingrowth of bone between the expansion portions and the body or into the internal section of the body is substantially avoided when the expansion portions are in the expanded configuration.

The fastener may be arranged such that a thickness of each of the expansion portions overlaps with the thickness of the body when the fastener is in the expanded configuration. Each expansion portion typically contacts the body along the length of the expansion portion (and typically also across the width) such that a gap is avoided when the expansion portion is in the expanded configuration. Alternatively or additionally, the fastener comprises an element, such as a layer or a fill material, which is arranged to cover or fill at least a portion of a gap between the expansion portion and the body or between adjacent expansion portions when the fastener is in the expanded configuration.

The fastener has a hollow interior region for receiving an actuating member that engages with the expansion portions and urges the expansion portions outwardly when the actuating member is moved into the interior region of the fastener.

In general, such a fastener may be inserted into a provided predrilled bore hole in bone as follows. The fastener is provided in a contracted state and engaged with a suitable tool that holds the fastener and prevents translational or rotational movement relative to the fastener. The tool is then used to insert the fastener into the predrilled bore hole. As will be described in further detail below, the fastener may comprise an actuating member. The tool is kept engaged with the fastener while the actuating member is inserted into the fastener to stop relative translational or rotational movement between the fastener and the bone. The actuating member is then inserted into a hollow space within the fastener along an axis of the fastener and moved towards a distal portion of the fastener. Alternatively, the fastener may be arranged such that the actuating member is rotated within the body of the fastener. In either case, one or more expansion portions urge outwardly during movement of the actuating member towards an expanded configuration in which the one or more expansion portions engage with the bore hole.

The fastener may be removed from the bore hole as follows. Initially the tool is engaged with the fastener in a manner such that rotational or translational movement of the fastener relative to the tool is prevented. The tool will also prevent translational and rotational movement of the fastener relative to the bone. The actuating member is then removed either by rotational movement or translational movement along the axis of the fastener whereby the one or more expansion portions contract into the contracted configuration so that the fastener can be removed from the bore hole. In an alternative variation which will be described in further detail below, the actuating member may also function as a removal member and may engage with the one or more expansion portions to move the one or more expansion portions to the contracted configuration.

Specific examples of the fastener will now be described with reference to FIGS. 1 to 16.

Referring initially to FIGS. 1 (a) and (b), there is shown an expandable fastener 10 for fastening when positioned in a bore hole in bone. The fastener 10 has a body 14 which has an axis A and multiple levels L1, L2, L3 and L4 at which expansion portions 16 are positioned. Each expansion portion 16 is moveable between a contracted configuration and an expanded configuration of the fastener 10. FIG. 1 (a) shows the expansion portion 16 in a contracted configuration and FIG. 1(b) shows the expansion portion in an expanded configuration.

In use, each expansion portion 16 urges outwardly from the body 14 towards the bone surrounding the bore hole (not shown). In this embodiment, the fastener 10 has a substantially circular cross-sectional shape in a plane that is transversal to the axis A. The fastener 10 is formed from bio-compatible materials.

Further, the body 14 of the fastener 10 has a threaded or corrugated outer surface along its length and at least a portion of the length of the expansion portions comprises a threaded or corrugated outer surface.

Figure 2:
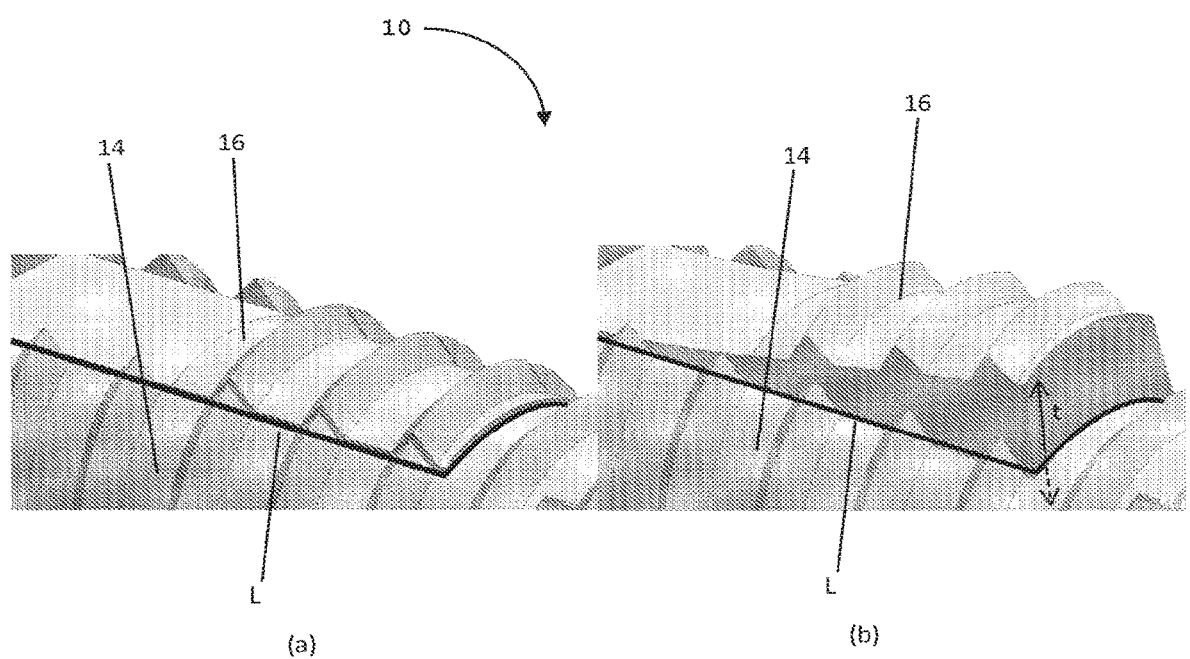
FIGS. 2 (a) and (b) show a portion of the fastener shown in FIG. 1.

Referring now to FIGS. 2 (a) and (b), there is shown a portion of the fastener 10 with the expansion portion 16 in the contracted configuration (a) and in the expanded configuration (b). The expansion portion 16 is arranged to urge from a contracted configuration outwardly away from the body 14 such that at least a portion of the thickness "t" the expansion portion 16 overlaps with a portion of the body 14 along the length "L" of the expansion portion 16. In one specific embodiment the expansion portion overlaps with the body and contacts the body such that a gap between the expansion portion and the body is substantially or even entirely avoided.

Figure 3:
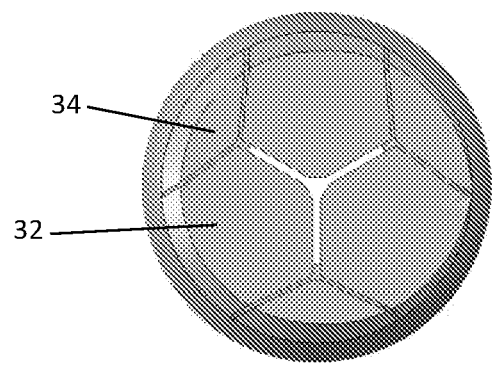
FIGS. 3 (a) to (c) show cross-sectional views of a fastener in accordance with an embodiment of the present invention.
Figure 3:
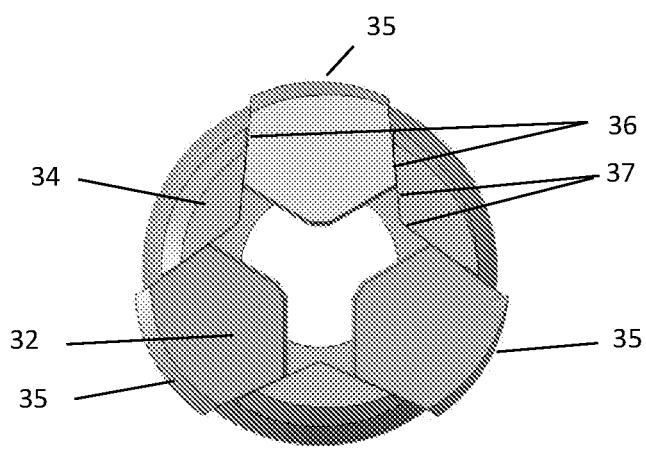
Figure 3:
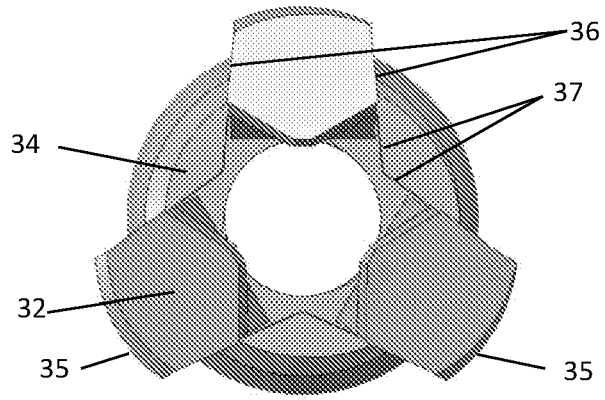

Referring now to FIG. 3, there are shown cross-sectional views of a fastener 30 in accordance with a further embodiment of the present invention. FIG. 3 (a) shows the fastener 30 in the contracted configuration, FIG. 3 (b) shows the fastener 30 in an intermediate configuration and FIG. 3(c) shows the fastener 30 in an expanded configuration. Expansion portions 32 are positioned between body portions 34 and have arc-shaped end surfaces 35 at which they contact the bone when in use. The body portions 34 have wedge-shaped contact surfaces 37 that wedge against the expansion portions 32 at contact surfaces 36 when the expansion portions 32 are in the expanded configuration.

Figure 4:
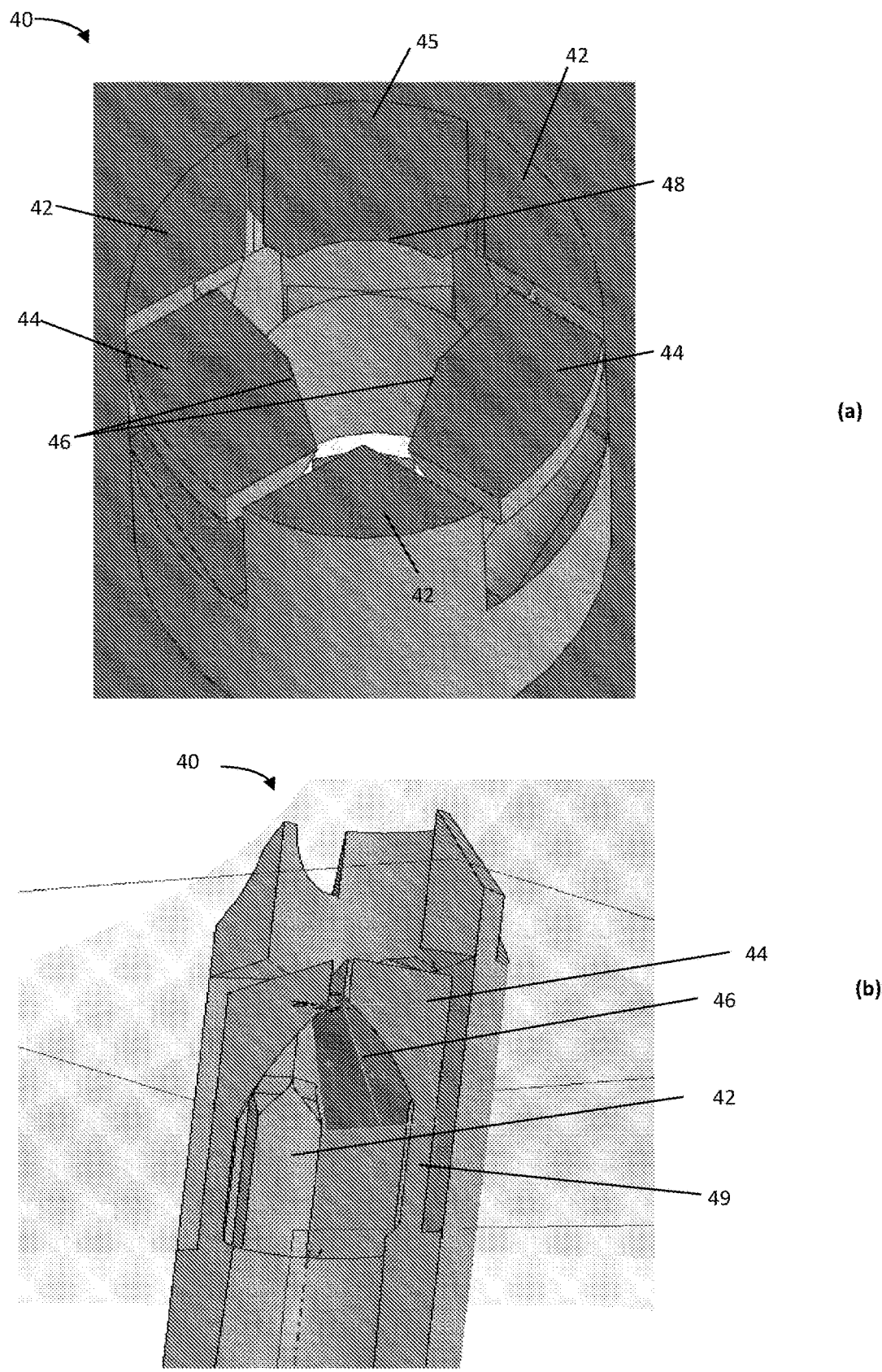
FIGS. 4 (a) and (b) show perspective cross-sectional views of portions of a fastener in accordance with an embodiment of the present invention.

FIG. 4 (a) shows a perspective cross-sectional view of a fastener 40 in accordance with a further embodiment of the present invention. The fastener 40 comprises body portions 42 and expansion portions 44 and 45. The expansion portions 44 and 45 have inner actuating surfaces 46 and 48, respectively. The expansion portions 44 and 45 urge outwardly when an actuating member (not shown) is received along an axis of the fastener 40 and urges against the actuating surfaces 46, 48, respectively. The actuating surface 46 of each expansion portion 44 is in this embodiment tapered to a tip (or may for example be convexly curved). In contrast, the actuating surfaces 48 of the expansion portion 45 is instead concavely curved such that a thickness of the expansion portion 45 at the side portions of the expansion portion 45 is increased compared with that of the expansion portion 44. Side portions of the expansion portions 44, 45 overlap with surfaces of the body 42 in either embodiment at least along a portion of the length of the expansion portions 44, 45 when the expansion portions 44, 45 are in the expanded configuration. However, because the actuating surfaces 48 of the expansion portions 45 is indented or concavely shaped and the thickness is increased at the side portions of the expansion portions 45, the expansion portions 45 can expand further without formation of a gap between the expansion portions 45 and the body 42 compared to expansion portions 44 with convexly shaped actuating surfaces, which reduces the likelihood of ingrowth of bone between each expansion portion 45 and the body 42 when the expansion portions 45 are in the expanded configuration.

In a variation of the above described embodiment the expansion portions have a thickness that is tapered in a direction around the axis of the fastener such that, when the expansion portions are in the expanded configuration, each expansion portion projects at one side portion further away from the axis than at an opposite second side portion. This embodiment provides the advantage that the contraction of the expansion portions is facilitated when the actuating member is removed and the fastener is rotated about the axis in a direction towards the thinner side portions of the expansion portions.

In general, each expansion portion has a bending region at which the material is thinner and at which the expansion portion predominantly bends when the expansion portion moves into the expanded configuration. Further, each expansion portion has an actuating surface that is sloped inwardly. The bending section should be as short as practical for providing elastic or substantially elastic deformation. A shorter bending section allows more expansions per unit length, which increases fixation strength. A shorter bending section also provides a stiffer spring-back force, which helps removability. Further, a shorter bending section also increases an expansion angle, which further increases fixation strength.

FIG. 4 (*b*) shows a cross-sectional perspective side view of a portion of the fastener 40. The Figure shows a bending region 49 and a sloped actuating surface 46 of the expansion portion 44. As mentioned above, it is advantageous to design the bending region of an expansion portion relatively short. Further, it is advantageous to design an upper region with the actuating surface relatively long and/or the slope of the actuating surface relatively gradual and extending along a relatively large length portion as then, when the expansion portion 44 is in the expanded configuration, the thickness of the side portions of expansion portion 44 overlaps along a longer length portion (or along the entire length) of the expansion portion 44 to avoid any gap.

Figure 5:
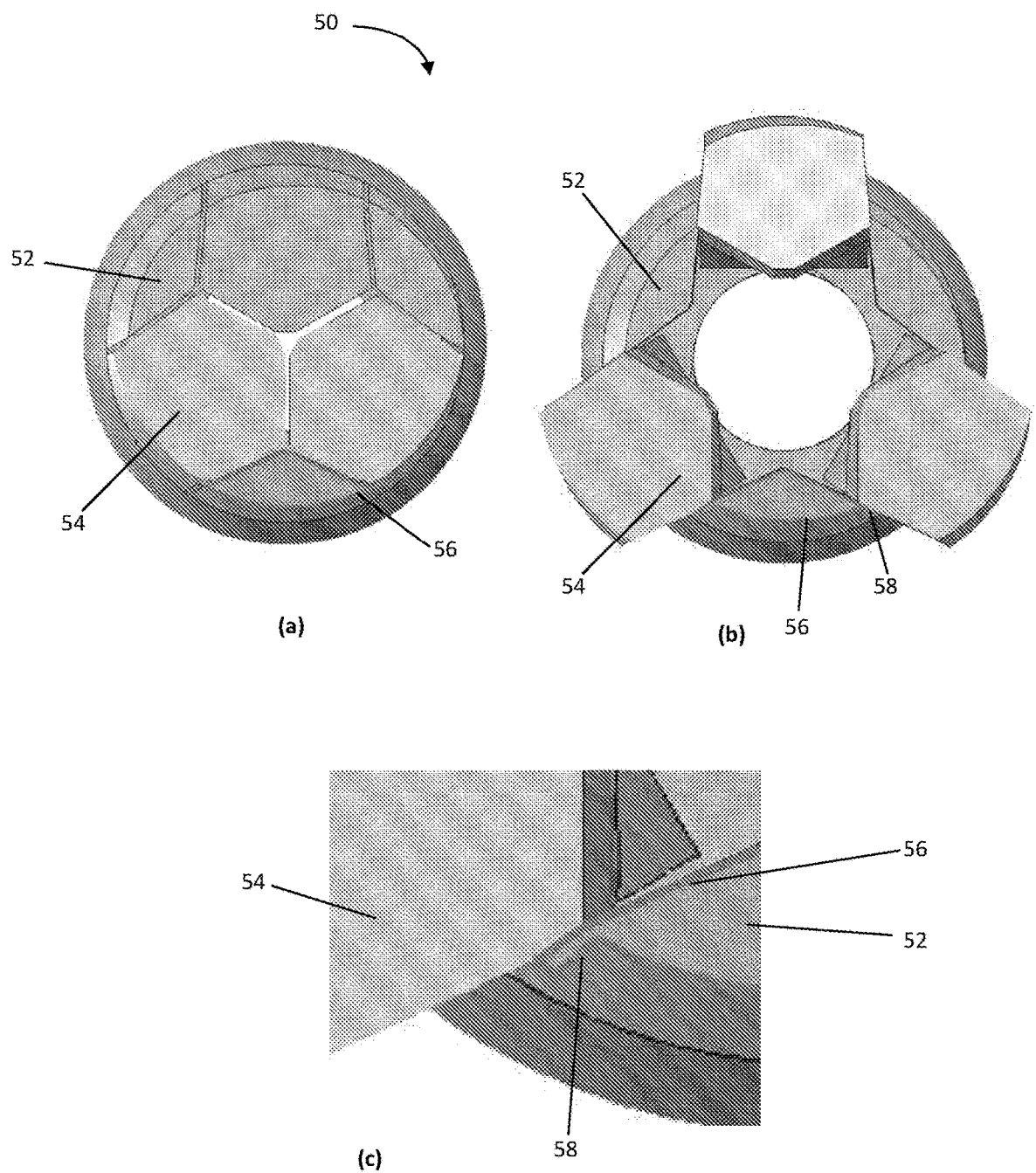
FIG. 5 shows cross-sectional views of a fastener in accordance with an embodiment of the present invention, (a) in a contracted configuration, and (b) and (c) in an expanded configuration.

FIG. 5 shows cross-sectional views of a fastener 50 in (a) contracted configuration and (b) expanded configuration in accordance with a further embodiment of the present invention.

The fastener 50 comprises a body 52 and expansion portions 54. In this example, the surface of the body 52 comprises an outer thin deformable layer of material 56 that is arranged such that, when the expansion portions 54 urge outwardly, contact surfaces of the body 52 fractionally engage with sidewalls of the expansion portions 54 thereby allowing the outer thin deformable layer of material 56 to deform and fill or overlap at least a portion of a gap that may otherwise form between the expansion portions 54 and the body 52. This results in accumulation of material, which is schematically indicated in FIG. 5(*c*) by a "lip" 58 that overlaps a portion of the expansion portion 54. The outer thin deformable layer of material may, for example be formed from the same metallic material as the material comprising the body 52, and may possibly be formed from titanium. The outer thin deformable layer of material surrounding the body 52 may be an extension of the body 52, built in during the manufacturing process.

A person skilled in the art will appreciate that alternatively portions of the expansion portion 54 may comprise this outer thin deformable layer of material.

Figure 6:
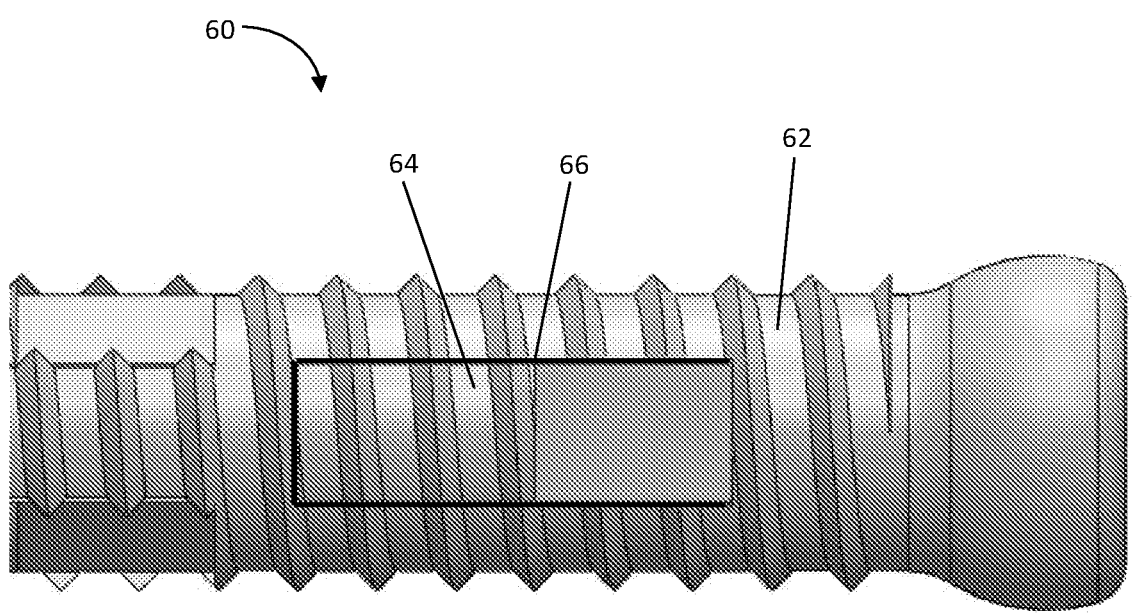
FIG. 6 shows a side view of a fastener in accordance with a further embodiment of the present invention.

FIG. 6 shows a side view of a fastener 60 comprising a body 62 and an expansion portion 64. In this example, a sealant 66 is injected in the areas in which bone ingrowth is not desirable, such as between the body 62 and the expansion portion 64. The sealant 66 is squeezed between the body 62 and the expansion portion 64 when the expansion portion 64 urges from a contracted configuration to an expanded configuration, so as to cover or fill a gap between the body 62 and the expansion portion 64 and thereby avoid ingrowth of bone between the body 62 and the expansion portion 64. The sealant 66 is in this embodiment a polymeric or an elastomeric compound, and may be non-viscous. The sealant 66 may also comprise a substance that inhibits growth of bone at the sealant and thereby inhibits ingrowth of bone.

Figure 7:
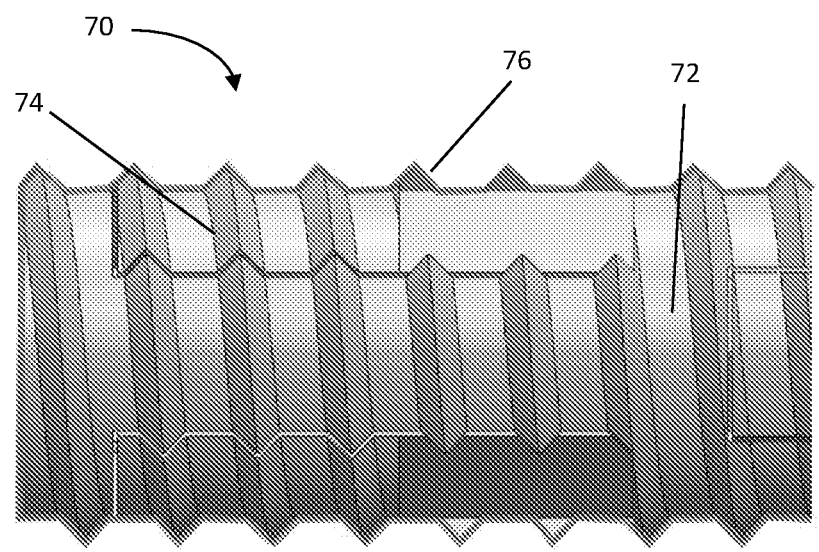
FIG. 7 shows a side view of a fastener in accordance with an embodiment of the present invention.

FIG. 7 shows a side view of a fastener 70 comprising a body 72 and an expansion portion 74 in accordance with an embodiment of the present invention. An outer surface of the fastener 70 is coated with a thin membrane 76. The thin membrane 76 is arranged to stretch as the expansion portion 74 moves from a contracted to an expanded configuration, thereby covering any gap and avoiding the undesirable ingrowth of bone when the expansion portion 74 is in the expanded configuration. The thin membrane 76 is in this embodiment a resilient elastomer such as silicone rubber.

Figure 8:
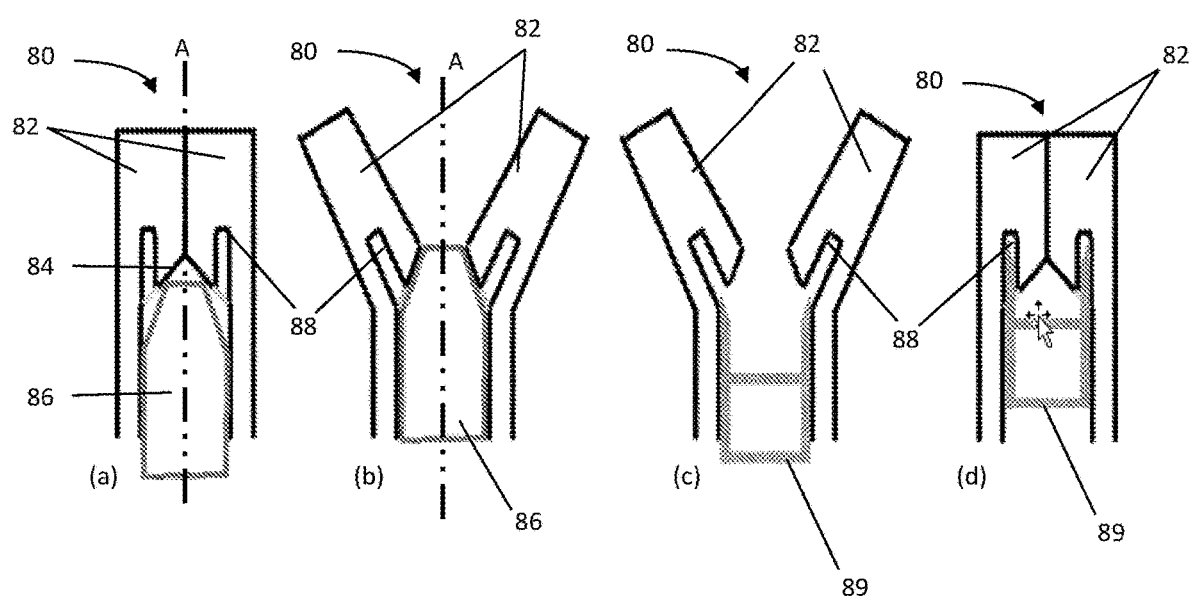
FIGS. 8(a) to (d) show cross-sectional views of portions of a fastener in accordance with an embodiment of the present invention.

FIGS. 8(*a*) to (*d*) show section views of a fastener 80. The fastener comprises expansion portions 82. In this embodiment, the expansion portions 82 have actuating surfaces 84 that are arranged to receive an actuating member 86 along an axis A of the fastener 80 whereby the expansion portions 82 are urged outwardly away from the axis A as seen in FIG. 8(*b*). The expansion portions 82 having actuating surfaces 84 are also arranged to urge inwardly from the bone towards the axis of the fastener 80 when the actuating member 86 is removed whereby the fastener 80 moves to the contracted configuration, such a configuration illustrated in FIG. 8(*a*). The expansion portions 82 are structured such that, when the actuating member 86 is received or removed, the expansion portions 82 urge elastically outwardly and inwardly, respectively.

If an expansion portion 82 fails to contract, a removal element 89 that couples with the fastener 80 may be used. The expansion portions 82 comprise in this embodiment holes 88 that taper inwardly. The removal element 89 comprises projections that are arranged for engagement with the expansion portions 82 and within the holes 88 of the expansion portions 82 such that when the removal element 89 has engaged with the expansion portions 82 in the expanded configuration as shown in FIG. 8(*c*) and is pushed forwardly, the expansion portions 82 are moved inwardly and the fastener 80 is moved to a contracted configuration as shown in FIG. 8(*d*).

Figure 9:
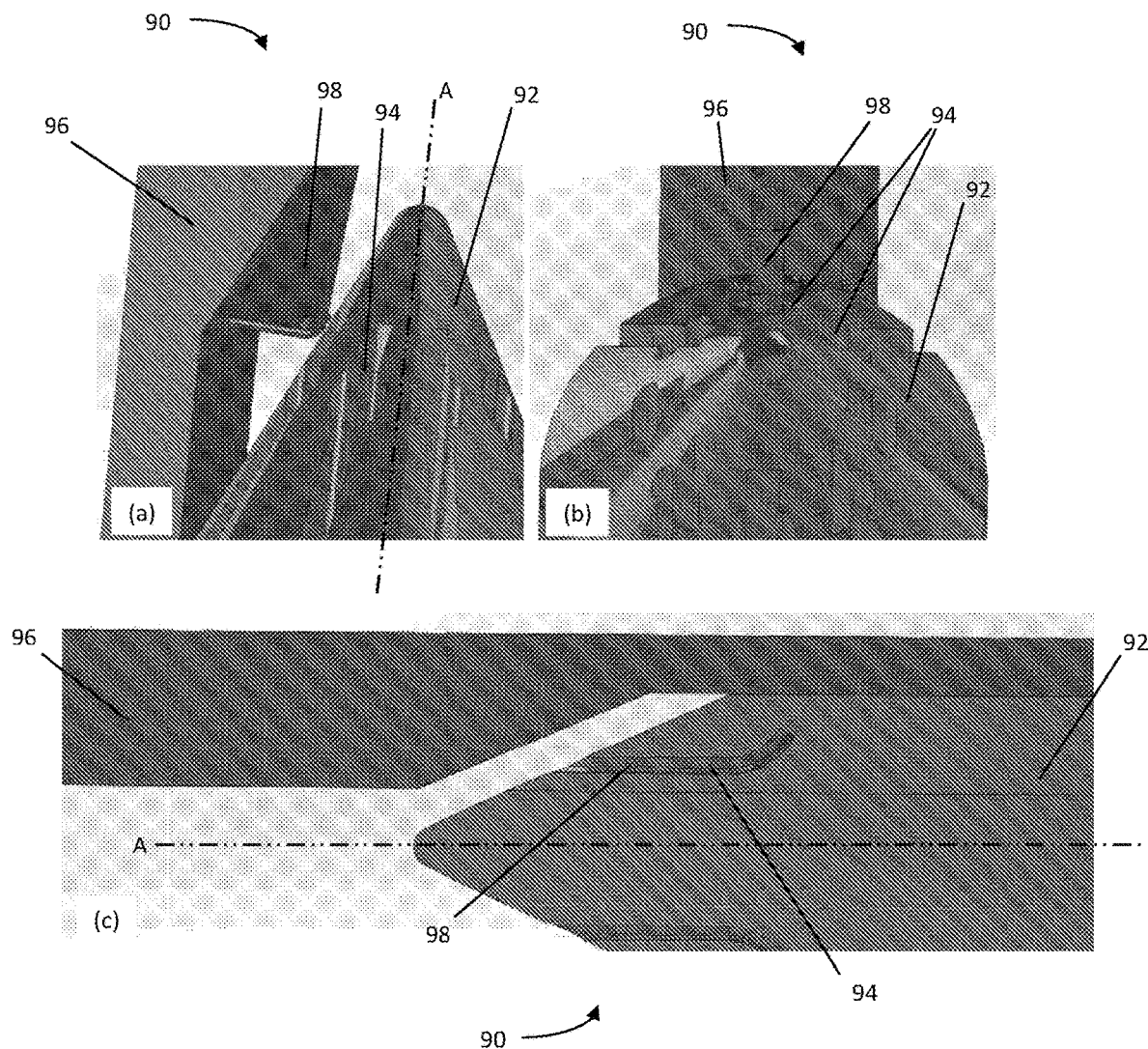
FIGS. 9(a) and (b) show perspective views of an end portion of an expansion portion and an end portion of a removal element in accordance with an embodiment of the present invention.
FIG. 9(c) shows a cross-sectional view of portions of an expansion portion and a removal element in accordance with an embodiment of the present invention.

FIGS. 9(*a*), (*b*) and (*c*) show portions of a fastener 90 in accordance with a further embodiment of the present invention. The fastener 90 comprises an actuating member 92 that functions as a removal element and has recesses 94. The fastener 90 further comprises the expansion portion 96 that has an engaging portion 98. The actuating member 92 and the expansion portion 96 are arranged such that recesses 94 engage with the engaging portion 98 of the expansion portion 96 when the actuating member 92 is received along the axis A and urges against the expansion portion 96. As the expansion portion 96 and the actuating member 92 are engaged, the expansion portion 96 moves outwardly when the actuating member 92 is inserted and moves inwardly from the bone surrounding the bore hole to the body when the actuating member 92 is retracted.

Figure 10:
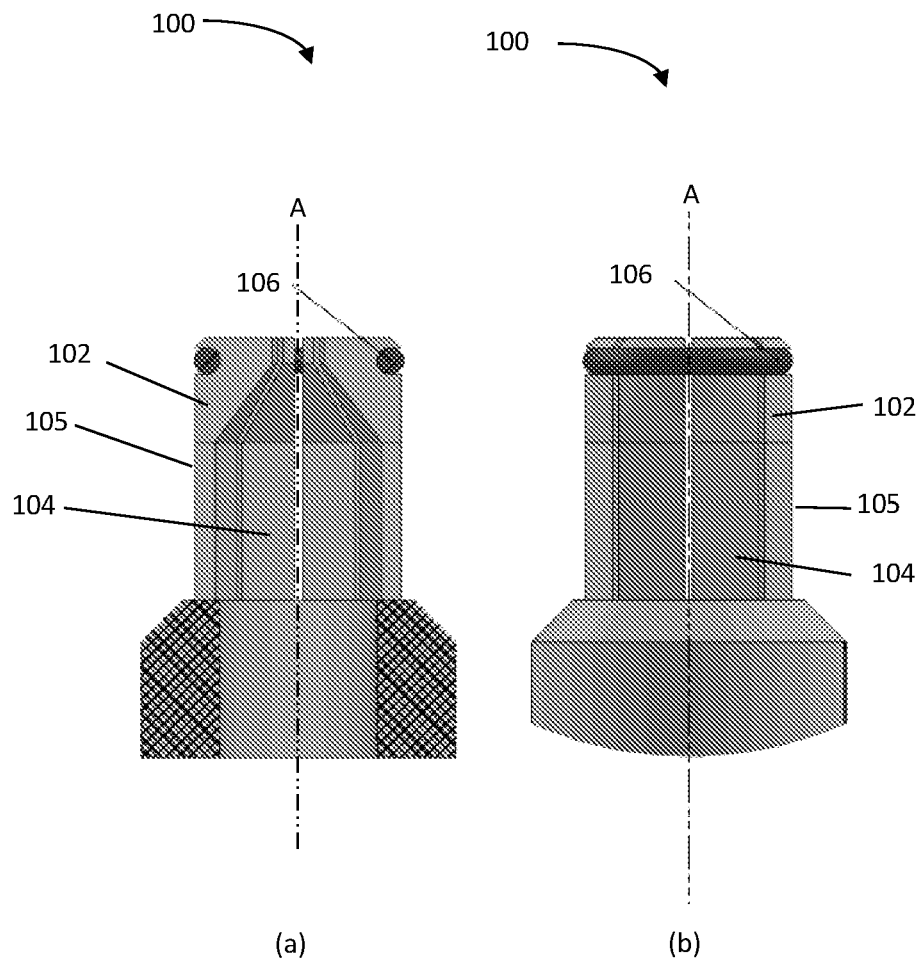
FIG. 10(a) shows a cross-sectional view of a fastener in accordance with an embodiment of the present invention.
FIG. 10(b) shows a side view of the fastener of FIG. 10(a)

FIG. 10 shows (a) a cross-sectional view and (b) a side view of a fastener 100 comprising a body 102, an expansion portion 104 and a removal element 106 coupled to a portion of the outer surface 105 of the fastener 100. In this embodiment the removal element 106 is coupled to the body 102 and the expansion portion 104 to increase the contraction force and induce contraction of the expansion portion 104 when the actuation member is removed from an interior of the fastener 100. The removal element 106 is an elastic ring, such as an O-ring formed from a polymeric material. Alternatively, the removal element 106 may also be a suitable spring clip, such as a spring clip formed from a metallic material (such as titanium).

Figure 11:
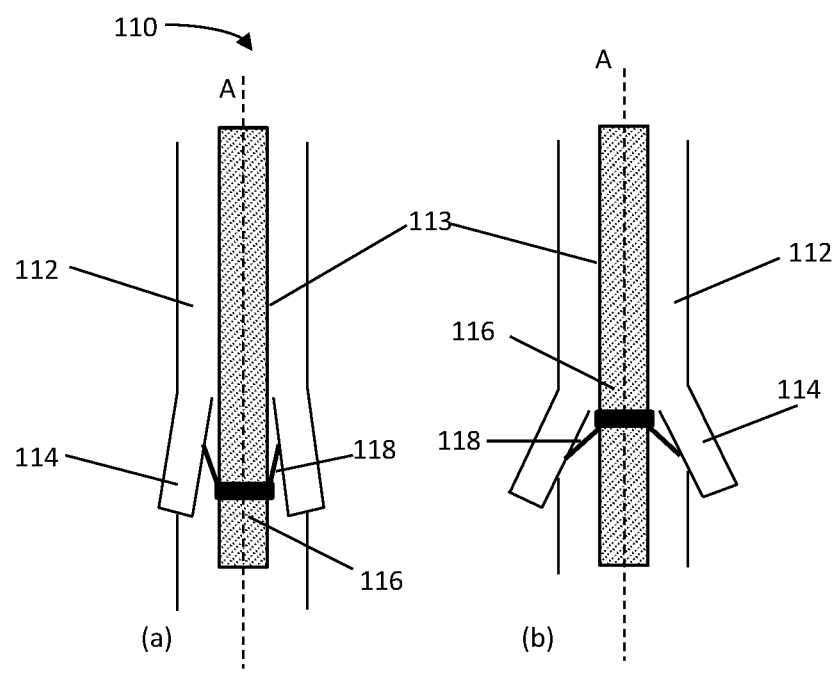
FIG. 11 shows a cross-sectional view of a fastener in accordance with an embodiment of the present invention.

FIG. 11 shows cross-sectional views of a fastener 110 comprising a body 112 and two opposite expansion portions 114. The expansion portions 114 are coupled to an actuating element 113 that also functions as a removal element. The actuating element 113 comprises a central rod 116 connected to stiff radial linkages 118. The actuating element 113 is arranged and the linkages are positioned such that the expansion portions 114 move between a contracted configuration (a) and an expanded configuration (b) when the actuating element 113 moves to different positions along the axis A of the fastener 110.

Figure 12:
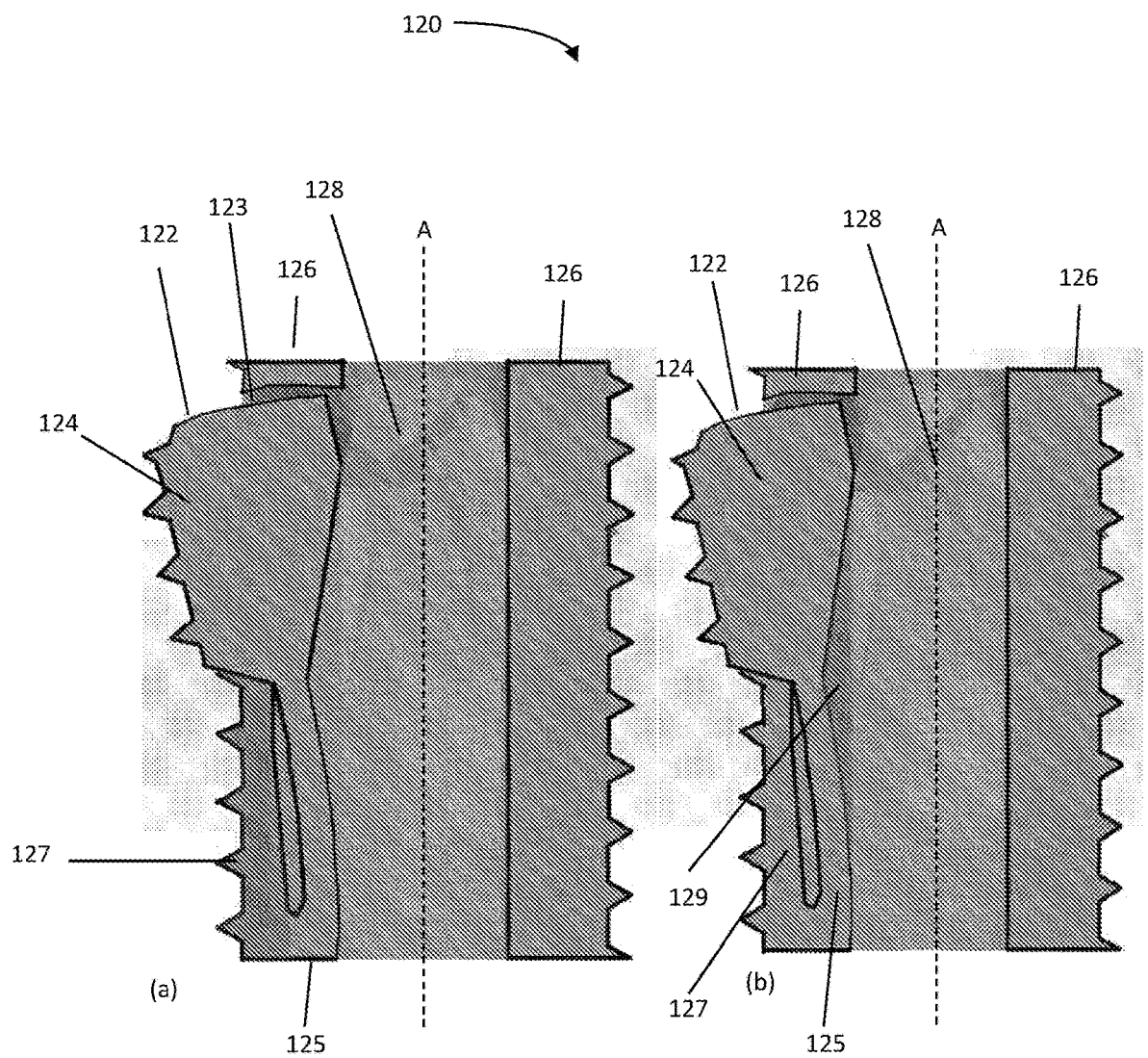
FIGS. 12(a) and (b) show cross-sectional views of portions of a fastener in accordance with an embodiment of the present invention.

FIGS. 12(*a*) and (*b*) show cross-sectional views of portions of a fastener 120 in accordance with an embodiment of the present invention. In this embodiment, an expansion portion 122 has an end surface 123 that is substantially arc shaped such that, when the expansion portion 122 is in the expanded configuration, interference of the expansion portion 122 with the surrounding growing bone (not shown) is minimised. Further, the expansion portion 122 comprises an upper section 124 with a threaded or corrugated outer surface, and a bending section 125 at which the material is thinner than the material of the upper section 124 and at which the expansion portion 122 predominantly bends when the expansion portion 122 urges towards an expanded configuration. The bending section 124 is positioned inside the outer periphery of a body 126 and is overlapped by a portion of the body 126.

This embodiment allows a greater expansion angle of the expansion portion 122 while substantially avoiding any gap between the body 126 and the expansion portion 122 when the expansion portion 122 is in the expanded configuration, which further increases the fixation strength of the fastener 120.

This embodiment further allows a section 127 with a threaded or corrugated outer surface to be positioned at the outer surface of the bending section 125 to cover or fill a gap at the bending section 125 between the body 126 and the expansion portion 122 when the expansion portion 122 is in the expanded configuration. Thereby, ingrowth of bone between the body 126 and the expansion portion 122 when the expansion portion 122 is in the expanded configuration is prevented in the area surrounding the bending section 125 and the threaded or corrugated outer surface of the additional section 127 further increases the fixation strength of the fastener 120 in the bore hole of a bone (not shown).

In this embodiment, when an actuating member 128 is received along an axis A of the fastener 120 and urges the expansion portion 122 outwardly, it is also possible to fill in the gap along the axis A of the body 126 of the fastener 120 with a deformable material 129 infused with an antibacterial substance to prevent growth of bacteria along the axis of the body 126 of the fastener 120 when the expansion portion 122 is in the expanded configuration. The deformable material 129 may comprise rubber.

Figure 13:
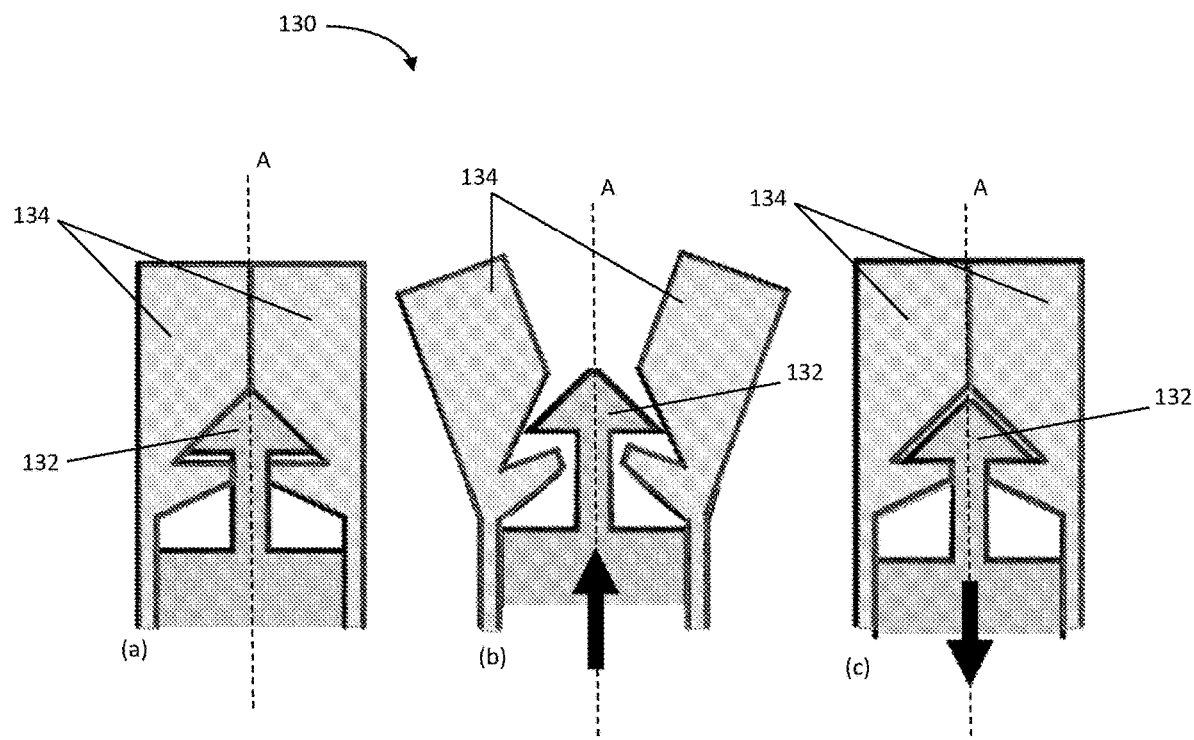
FIG. 13 shows cross-sectional views of a fastener in accordance with an embodiment of the present invention, (a) in a contracted configuration, (b) in an expanded configuration, and (c) in a contracted configuration.

FIG. 13 shows cross-sectional views of a fastener 130 in accordance with an embodiment of the present invention, (a) in a contracted configuration, (b) in an expanded configuration, and (c) in a contracted configuration. In this embodiment, an actuating member 132 functions as a removal element. The actuating member 132 engages with expansion portions 134 in a "tulip" design (a), such that the expansion portions 134 are forced to move from an expanded (b) to a contracted (c) configuration when the actuating member 132 is moved in a direction away from the bore hole along an axis A of the fastener 130.

Figure 14:
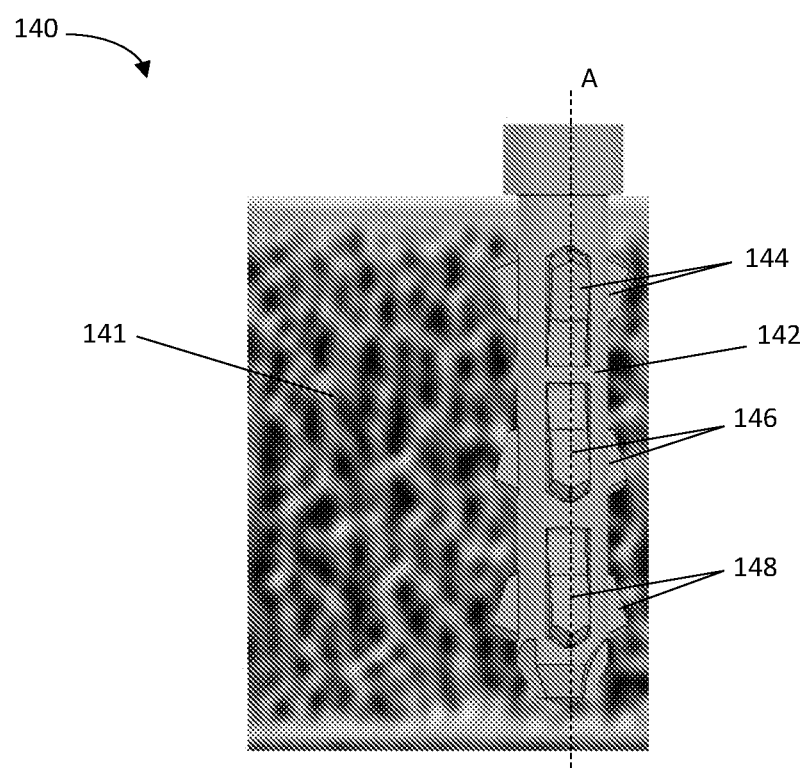
FIG. 14 shows a side view of a fastener in accordance with an embodiment of the present invention.

FIG. 14 shows a side view of a fastener 140 in an expanded configuration when inserted in a bore hole of a bone 141, in accordance with an embodiment of the present invention. The fastener 140 comprises a body 142 and three levels of expansion portions 144, 146, and 148, distributed along the length of the fastener 140, for fixation in the bore hole of a bone 141. In this embodiment, at least two levels of expansion portions such as 144 and 146 are facing in opposite directions along the axis A of the body 142 (the expansion portions 144 are rotated by 180 degrees compares to the expansion portions 146). The expansion portions 144, 146, and 148 urge outwardly from the body 142 towards the bone 141, when an actuating member (not shown) is received along the axis A of the body 142 and urges against the actuating surface portions (not shown) of the expansion portions 144, 146 and 148. The two levels of expansion portions 144 and 146 that face in opposite directions allow increasing the fixation strength of the fastener 140, when in the expanded configuration, onto the bone 141 surrounding the bore hole, in particular where the bone 141 is hard and dense such as cortical bone, which is harder and denser than cancellous bone.

Figure 15:
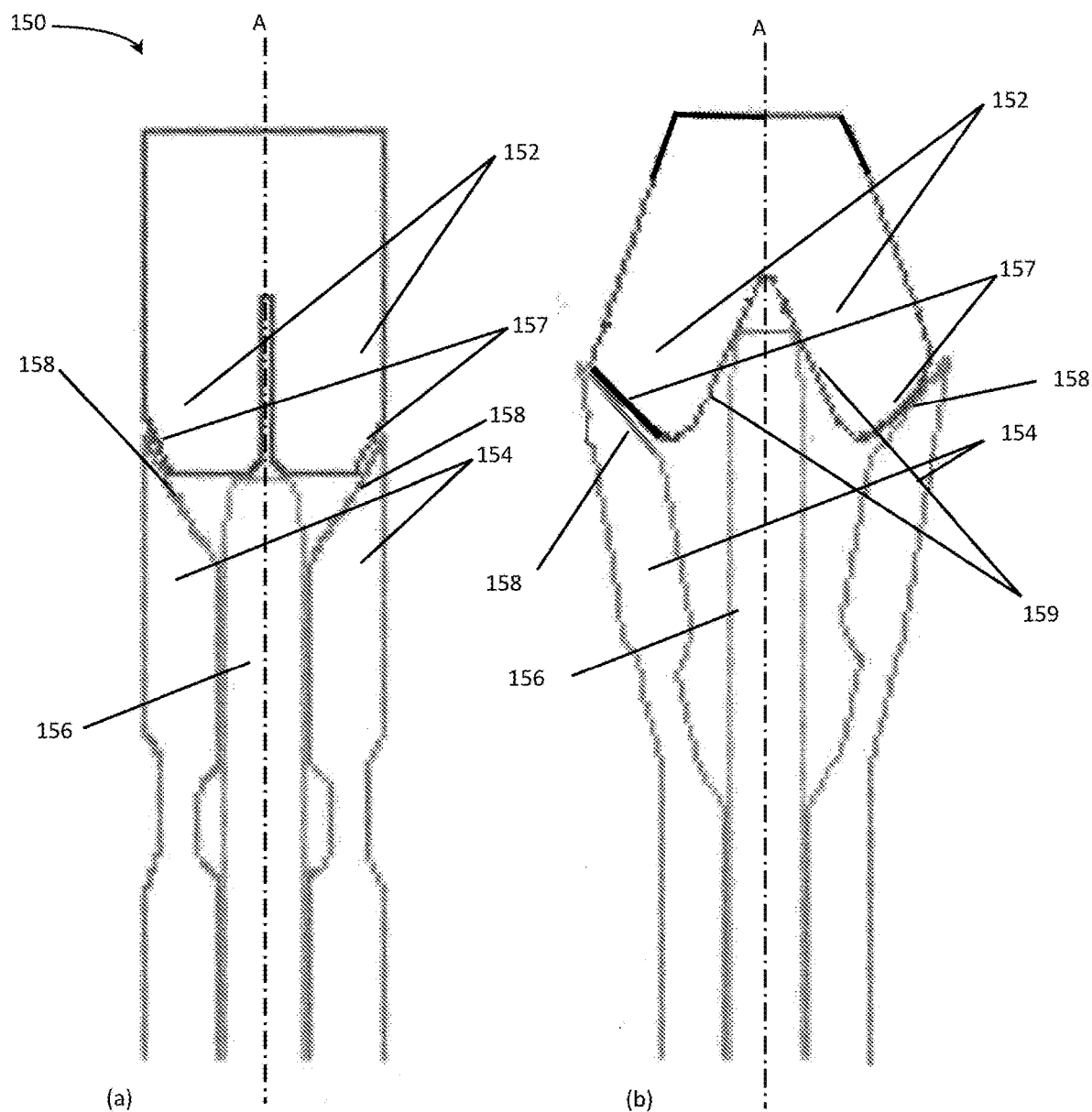
FIG. 15 shows cross-sectional views of a fastener in accordance with another embodiment of the present invention (a) in a contracted configuration, and (b) in an expanded configuration.

FIG. 15 shows cross-sectional views of a fastener 150 in in accordance with another embodiment of the present invention, (a) in the contracted configuration and (b) in the expanded configuration. In this embodiment, two pairs of expansion portions 152 and 154 are positioned at different longitudinal positions along the axis A of the fastener 150. The pair of expansion portions 152 is oriented opposite to the pair of expansion portions 154 such that ends 157 of the expansion portions 152 oppose respective ends 158 of the expansion portions 154. The expansion portions 152 have actuating surfaces 159 that are arranged to receive an actuating member 156 along the axis A of the fastener 150, from a proximal end of the expansion portions 154 towards the ends 157 of the expansion portions 152, whereby the expansion portions 152 are urged outwardly away from the axis A. The ends 157 of the expansion portions 152 contact the ends 158 of the expansion portions 154 such that the expansion of the expansion portions 152 urges the expansion portions 154 outwardly. Further, when the actuating member 156 is removed, the expansion portions 154 elastically urge inwardly away from the bone (not shown) towards the axis A. The ends 157 and 158 are in contact such that the expansion portions 152 are urged inwardly together with the expansion portions 154 when the inwardly urged ends 158 move against the opposing ends 157. The pairs of expansion portions 152 and 154 urge outwardly towards an expanded configuration (b) in a manner such that a gap between the opposing ends 157 and 158 is substantially avoided.

Figure 16:
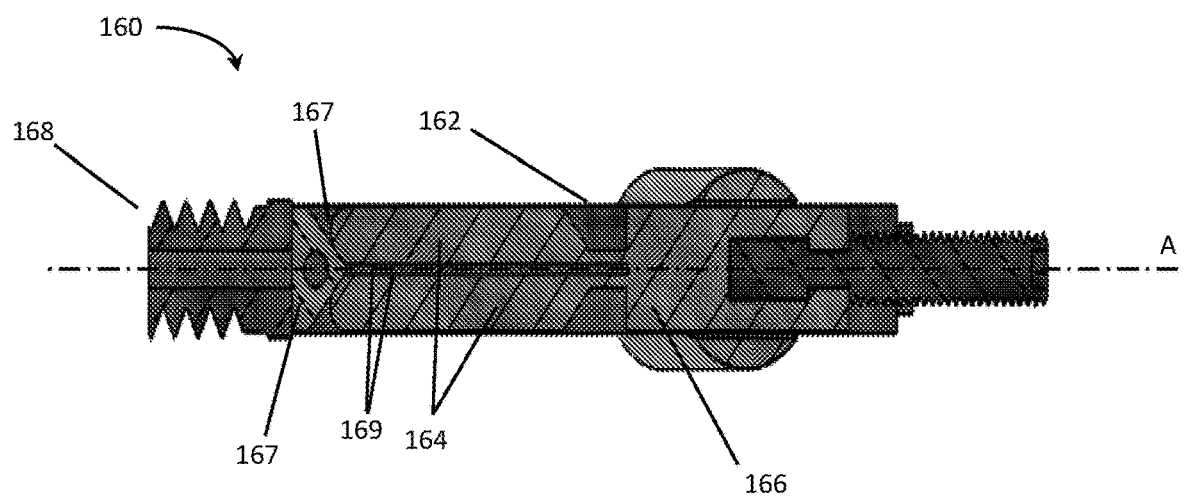
FIG. 16 shows cross-sectional views of a fastener in accordance with another embodiment of the present invention (a) in a contracted configuration, and (b) in an expanded configuration.
Figure 16:
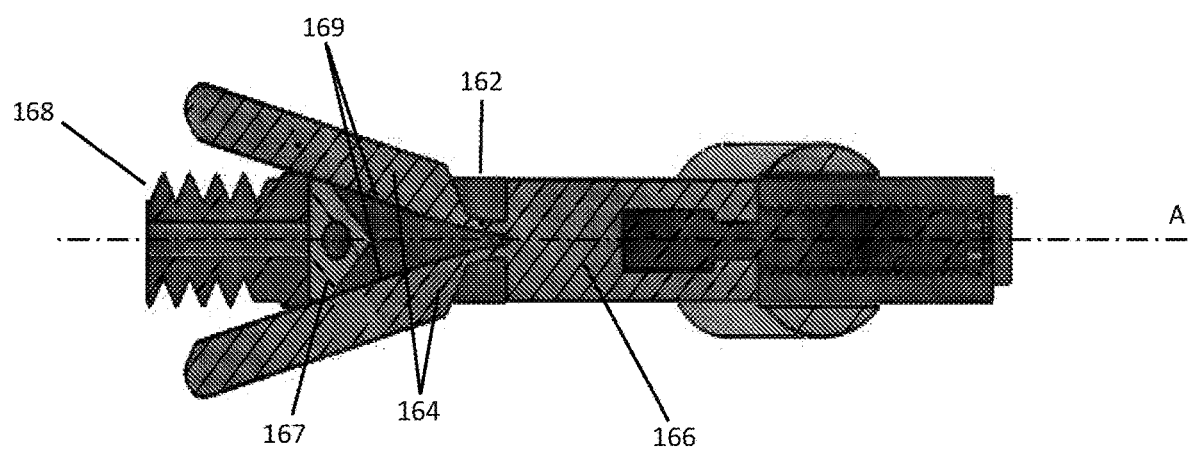

FIG. 16 shows cross-sectional views of a fastener 160 in accordance with another specific embodiment, (a) in the contracted configuration and (b) in the expanded configuration. In this specific embodiment, the fastener 160 comprises a body 162 and expansion portions 164, wherein the expansion portions 164 are part of an expansion member 166 positioned within the body 162, the expansion member 166 being moveable with the expansion portions 164 relative to the body 162 along an axis A of the body 162 of the fastener 160. The fastener 160 further comprises an actuating element 167 positioned at a distal end 168 of the fastener 160, and the expansion member 166 with the expansion portions 164 are moveable towards or away from the actuating element 167. The actuating element 167 has a tapered surface with an apex such that when the expansion member 166 with the expansion portions 164 are moved towards the distal end 168 of the fastener 160 and towards the actuating element 167, an outward urging of the expansion portions 164 is facilitated, and the expansion portions 164 are urged outwardly away from the axis A of the fastener 160 when the expansion member 166 with the expansion portions 164 are further moved towards the actuating element 167, which is received by actuating surfaces 169. The fastener 160 is thus transferred to an expanded configuration (b).

Further, when the expansion element 166 is moved away from the actuating element 167, the expansion portions 164 are urged to move inwardly and away from the actuating element 168, such that the fastener 160 is transferred to a contracted configuration (a).

Numerous variations and modifications will suggest themselves to persons skilled in the relevant art, in addition to those already described, without departing from the basic inventive concepts. All such variations and modifications are to be considered within the scope of the present invention, the nature of which is to be determined from the foregoing description. For example, the fasteners may not necessary have a substantially circular cross-sectional shape and may alternatively have any other suitable cross-sectional shape. Further, the fasteners may be formed from any suitable material.

The invention claimed is:

1. An expandable fastener for orthopaedic applications and arranged for fastening when positioned in a bore hole in bone, the fastener comprising:
   a body having an axis;
   an actuating element attached to the body at a distal end of the fastener; and
   an expansion portion moveable between a contracted configuration and an expanded configuration such that, in use, the expansion portion urges outwardly from the body towards the bone surrounding the bore hole, the expansion portion being part of an expansion member that is moveable relative to the body and towards or away from the actuating element along the axis of the body;
   wherein the fastener is arranged such that ingrowth of bone between the expansion portion and the body is substantially avoided when the expansion portion is in the expanded configuration; and
   wherein the fastener is arranged such that, when the expansion member is moved towards the distal end of the fastener and towards the actuating element and engages with the actuating element, further movement of the expansion member towards the actuating element urges the expansion portion of the expansion member away from the axis of the body to transfer the fastener into the expanded configuration.

2. The fastener of claim 1, wherein the fastener is arranged such that, when the fastener is in the expanded configuration, the expansion member is in contact with the body along at least a majority of a length of the expansion portion.

3. The fastener of claim 1 wherein the expansion portion is at least partially surrounded by the body when the expansion portion is in the expanded configuration and wherein a gap between the expansion portion and the body is substantially avoided such that ingrowth of bone is substantially avoided.

4. The fastener of claim 1 wherein any immediately adjacent surface regions of the expansion portion and the body are in direct contact with each other such that a gap between the adjacent surface regions is substantially avoided.

5. The fastener of claim 1 wherein the fastener is arranged such that at least a portion of a thickness of the expansion portion overlaps with a portion of the body along a length of the expansion portion when the fastener is in the expanded configuration.

6. The fastener of claim 1 comprising an element arranged to cover or fill at least a portion of a gap between the expansion portion and the body when the fastener is in the expanded configuration.

7. The fastener of claim 1 wherein the expansion member is separate from the body.

8. The fastener of claim 1 wherein the expansion portion has wedge-shaped contact surfaces that extend along at least a portion of a length of the expansion portion and wedge against the body at contact surfaces of the body when the fastener is in the expanded configuration.

9. The fastener of claim 1 wherein the expansion portion is one of a plurality of expansion portions.

10. The fastener of claim 9 comprising at least two pairs of expansion portions, wherein the expansion portions of one pair are oriented opposite to the expansion portions of another pair such that ends of the expansion portions of one pair oppose ends of the expansion portions of another pair, and wherein the expansion portions of the pairs are arranged to urge outwardly when the ends of the expansion portions of one pair are moved against the opposing ends of another pair.

11. The fastener of claim 1 wherein the expansion portion comprises a bending region at which the expansion portion predominantly bends when the expansion portion urges towards the expanded configuration and the bending region is positioned inside an outer periphery of the body and is at least partially overlapped by a portion of the body.

12. The fastener of claim 1 wherein at least portions of the body or the expansion portion comprises an outer deformable layer of a material, and is arranged such that, when the expansion portion urges outwardly, contact surfaces of the body or sidewalls of the expansion portion fractionally engage with each other thereby allowing the outer deformable layer of material to deform and fill or overlap at least a portion of a gap that may otherwise form between the expansion portion and the body.

13. The fastener of claim 1 comprising an outer elastic membrane arranged to overlay gaps that may otherwise form between the body and the expansion portion or between adjacent expansion portions when in the expanded configuration and thereby avoid ingrowth of bone.

14. The fastener of claim 1 comprising a material that is non-viscous and is positioned between the body and the expansion portion or between adjacent expansion portions so as to fill a gap.

15. The fastener of claim 1 wherein a deformable material is infused into an interior of the fastener and is an antibacterial substance arranged to substantially prevent formation or accumulation of bacteria.

16. The fastener of claim 1 comprising a coating that has chemical properties that substantially inhibit or reduce growth of bone at the coating such that the ingrowth of bone between the expansion portion and the body is reduced when the fastener is in the expanded configuration.

* * * * *